United States Patent [19]

Fraefel et al.

[11] Patent Number: 4,544,552

[45] Date of Patent: Oct. 1, 1985

[54] PROCESS FOR THE PREPARATION OF CELL AND TISSUE REGENERATING SUBSTANCES

[75] Inventors: Wolfgang Fraefel, Grolley; Roland Tschannen, Basel, both of Switzerland

[73] Assignee: Solco Basel AG, Basel, Switzerland

[21] Appl. No.: 498,468

[22] Filed: May 26, 1983

[30] Foreign Application Priority Data

May 28, 1982 [CH] Switzerland .................. 3328/82

[51] Int. Cl.$^4$ ............... A61K 31/70; A61K 35/14; C12N 5/00
[52] U.S. Cl. ............................. 514/23; 424/95; 424/101; 435/240; 435/241; 536/17.9; 536/53
[58] Field of Search .................. 424/95, 101, 180; 536/17.9, 53; 435/240, 241

[56] References Cited

U.S. PATENT DOCUMENTS 3,526,697  9/1970  Livingston .................. 424/95
3,672,954  6/1971  Grippa ........................ 424/95

OTHER PUBLICATIONS

Kirk–Othmer–Encyclo. Chem. Tech. vol. 12, (1954), pp. 670–680.
Hakomori–Ann. Rev. Biochem. vol. 52, (1981), pp. 733–764.

Primary Examiner—Sam Rosen
Attorney, Agent, or Firm—Ladas & Parry

[57] ABSTRACT

Glycolipids having cell- and tissue-regenerating properties are isolated from the blood or organ homogenates of mammals by subjecting the starting material to autolysis and dialysis against an alcoholic-aqueous medium. The glycolipids can be isolated, and purified, from the resulting crude product by precipitation with ethanol or extraction followed by chromatography. The process gives relatively high yields of active compounds; it is outstandingly suitable for industrial application.

8 Claims, No Drawings

PROCESS FOR THE PREPARATION OF CELL AND TISSUE REGENERATING SUBSTANCES

Certain compounds which occur in the organs and body fluids of mammals or can be extracted therefrom and which exert an accelerating effect on the healing of wounds have already been disclosed (European Patent Application No. 81102848.9, Publication No. 0,038,511). According to the publication mentioned, the active compounds extracted have, in particular, the structure of a glycosteroid or of a glycosphingolipid.

The glycosteroid is said to correspond to the following structural formula:

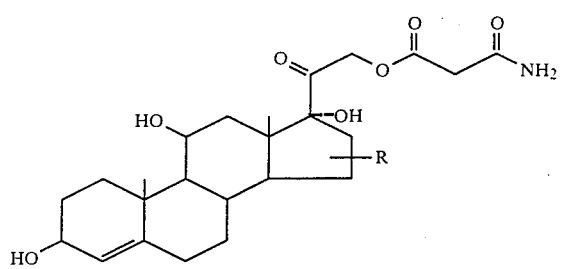

in which R denotes the radical of an oligosaccharide consisting of five sugar units.

The glycosphingolipid in turn is said to have the following structure:

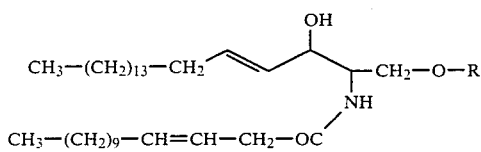

in which R denotes the radical of an oligosaccharide consisting of five sugar units.

These compounds have been isolated from organs, such as the heart, lung, muscles and spleen, and from body fluids, such as blood, plasma and serum. Mammals which produce the compounds are humans, pigs, horses, sheep and cattle.

The preparation process according to the patent application mentioned comprises, in particular, adsorption onto active charcoal (affinity chromatography) and extraction with 10–30% strength acetic acid, a second chromatography on a molecular sieve and elution with dilute acetic acid, and a third chromatography on silica gel and elution with a mixture of ethanol and methylene chloride or on silica gel coated with $C_8$-chains and elution with mixtures of acetic acid, ethanol and water.

It has now been found, surprisingly, that glycolipids having cell- and tissue-regenerating properties can be obtained from the same starting materials as those mentioned above but in a substantially higher yield if the starting material is first subjected to autolysis and dialysis against an alcoholic-aqueous medium. In fact, a crude product in which the desired active compounds are enriched in amazingly larger amounts than was the case in the process already known is thereby obtained.

However, during develepment of the process according to the invention, it has been found that the abovementioned glycosteroids do not have sufficient stability on therapeutic use to deserve further interest.

It has furthermore also been found that the glycolipids can be isolated from the above crude product in a significantly more simple manner by (A) precipitating them from an ethanolic solution at low temperature, for example at about −20° C., or (B) extracting them with an organic solvent which is water-immiscible or is water-miscible only to a limited extent, and chromatographing the product from stage (A) or (B) on silica gel or on an ion exchanger using a solvent of low polarity. If the extent of chromatographic separation is considered, a considerable advantage of the new process compared with the known process is evident from the necessity of a single chromatography operation, especially in the case of industrial use.

In marked contrast to the earlier process, the new process is in general outstandingly suitable for carrying out on an industrial scale, not least because the essential stages of autolysis and dialysis can be carried out simultaneously and continuously, in a countercurrent process.

The process according to the invention is characterised in that the blood or organ homogenate is subjected to autolysis and dialysis against an alcoholic-aqueous medium.

The invention is described in more detail below.

Of the abovementioned starting materials, blood and organ homogenates from mammals such as bovine or calf blood, especially the latter, are preferred.

As has been mentioned above, autolysis of the starting material and dialysis of the autolysate are first carried out. It is advantageous first to add a short-chain alcohol, preferably methanol or ethanol in a concentration of 10 to 30%, and a bacteriostatic agent, preferably methyl 4-hydroxybenzoate or propyl 4-hydroxybenzoate in a concentration of 0.1 to 0.0001%, to the starting material to dissolve the substances formed during the autolysis. The autolysis can be carried out by leaving the starting material to stand at a temperature from 4° C. to room temperature for a period of several hours to some days, for example for three days. However, it is more advantageous to carry out both measures simultaneously and continuously, in a countercurrent process, since the equilibrium on the side of the starting material is continuously shifted in favour of the autolysis reaction by continuous removal of the autolysis products. During the autolysis, intracellular catabolic enzymes, such as the lysosomes, are liberated, for example the cathepsins and other proteases, and furthermore nucleotidases, esterases, phosphatases and the like.

The substances with a molecular weight below 10,000, including the desired glycolipids, are present in the dialysate. At the same time as accelerating autolysis, dialysis thus effects removal of, in particular, those proteins which can lead to allergic reactions being triggered off during therapeutic use of the product. Advantageous media for taking up the substances during the dialysis are mixtures of water and lower aliphatic alcohols, for example methanol and ethanol. Particularly suitable mixtures consist of water and 10 to 30% by volume of ethanol, for example water with 15% by volume of ethanol.

If necessary, the crude product is intermediately protected for the subsequent isolation and separation measures. Quite generally, the same protective groups as those known for this purpose from peptide chemistry are suitable for this. The functional groups of the active compounds are thus blocked by selective introduction of protective groups, and the active compounds are converted into a more suitable form for extraction from the reaction mixture. After isolation and purification have been carried out, the protective groups are split off. Examples of suitable protective groups and the methods by which they are split off are the benzoyl group/splitting off by dilute alkali metal hydroxide solution; the benzyloxycarbonyl group/splitting off by hydrogen bromide in glacial acetic acid, trifluoroacetic acid or other organic solvents, hydrogen chloride in ethanol, trifluoroacetic acid under the influence of heat or metallic sodium in liquid ammonia; benzyl and p-toluenesulphonyl group/splitting off by sodium in liquid ammonia; and the tert.-butyl group/splitting off by hydrogen chloride in organic solvents, hydrogen bromide in glacial acetic acid, or trifluoroacetic acid. The tert.-butyl group can be introduced in a particularly elegant manner by acid-catalysed etherification with isobutene.

The glycolipids from the resulting dialysate can be isolated and purified (A) by precipitation in the cold from an ethanolic solution or (B) by extraction with certain organic, for example lipophilic, solvents followed by chromatography on an inorganic adsorbent or on an ion exchanger. Further purification by precipitation can advantageously be inserted between the extraction (B) and the chromatography.

The precipitation (A) is effected from an ethanolic solution at a temperature in the range from −15° to −25° C. It gives better yields of glycolipids, the higher the final concentration of ethanol. Advantageously, anhydrous ethanol is added to the dialysate in an amount such that a concentration thereof of at least 60% by volume is achieved; the best results are obtained with an end concentration of 90% by volume. The ethanolic solution formed is left to stand at the above temperature for several hours.

The solid substances can be separated off by filtration, centrifugation or sedimentation and decanting. The product is then dried under mild conditions, that is to say at a temperature of at most 37° C. Drying is effected by warming or in vacuo, or by both measures simultaneously.

The dialysate is used for the extraction (B) either in dried, solid form or in the form of an aqueous solution or a solution in an organic solvent. A solvent or solvent mixture which is water-immiscible or water-miscible only to a limited extent is used for the extraction. Particularly suitable solvents are ethers, such as diethyl ether and tetrahydrofuran, hydrocarbons, such as pentane, hexane, petroleum ether and benzene, halogenated hydrocarbons, such as chloroform, methylene chloride, carbon tetrachloride, 1,2-dichloroethane and mixtures of chloroform and methanol, alcohols, such as butanol and amyl alcohol, and carboxylic acid esters, such as ethyl acetate and butyl acetate.

Separation of the starting material into liquid/liquid phases or liquid/solid phases and thus separation of the constituents into substances of low polarity or apolar substances and polar or ionic substances is achieved by this extraction. The desired glycolipids pass into the organic, lesser polar phase. After separation from the other liquid phase or from the solid phase, the organic phase is dried under mild conditions, as has already been described above.

The extraction is preferably followed by precipitation of the glycolipids on the basis of their particular solubility in an aqueous solution of a metal salt and either acetone, diethyl ether, a mixture of both, or ethanol at a temperature in the range from −15° to −25° C. The aqueous solution contains the salt of a monovalent to pentavalent metal, preferably the metal salt of an inorganic acid. Magnesium chloride, calcium chloride, sodium chloride, potassium chloride, ammonium sulphate, sodium sulphate, potassium sulphate, sodium nitrate, disodium hydrogen phosphate and sodium dihydrogen phosphate are particularly suitable. The aqueous solution can have any desired concentration, up to saturation. The residue which remains on drying is now suspended or dissolved in this solution.

Although mixtures of acetone and diethyl ether can be used, the use of acetone or diethyl ether by itself, or of ethanol in the cold is preferred. Up to several times the volume of this solution is added to the suspension or solution first formed and all the components are mixed. The precipitate thereby formed contains the glycolipids; it is separated off from the liquid phase, which can be effected by filtration, centrifugation or sedimentation and decanting. The product is then dried under mild conditions. This procedure forms a first embodiment of the precipitation stage.

When the solubility conditions for precipitation of the glycolipids from the mixture of acetone or ether, or ethanol in the cold, and the aqueous metal salt solution are reached, the desired precipitation takes place. As the case may be, the product obtained by phase separation contains a sufficient concentration of salts - especially if the starting material is blood - for the precipitation to be effected merely by addition of acetone or ethanol, or ethanol in the cold. This procedure, in which no particular addition of a metal salt or a metal salt solution takes place, forms a second embodiment of the precipitation stage.

According to a third embodiment, it is even possible to carry out the extraction and the precipitation in the same operation. Thus, the dialysate can be treated with a mixture of the above organic solvent which is water-immiscible or water-miscible only to a limited extent and acetone or ether in a volume ratio with one another and in an amount depending on the volume and the metal salt concentration of the dialysate, and a precipitate containing the glycolipids is thereby obtained. The precipitate is separated off from the liquid phases, as described above, and dried under mild conditions.

In the last process stage, the product obtained from the precipitation with ethanol (A) or the extraction (B) is purified by chromatography. Inorganic adsorbents, in particular silica gel or a mixture of silica gel and a metal oxide or a salt of an inorganic acid, for example the commercially available mixtures of silica gel and aluminium oxide, magnesium oxide or magnesium sulphate, and also ion exchangers, in particular basic and acidic cellulose derivatives, such as diethylaminoethanecellulose, carboxymethylcellulose or sulphopropylcellulose, are suitable for this.

The product is first dissolved in an organic solvent of low polarity. Particularly suitable solvents are methanol, mixtures of methanol and chloroform and of ethanol and chloroform, and also ethyl acetate and mixtures of methanol, chloroform and a little water. The solution is introduced onto a chromatography column which has been filled under anhydrous conditions with the adsorbent in the same solvent or another of the abovementioned solvents. The same solvent or solvent mixture can be used for elution; however, it is also possible to use a solvent mixture of increasing polarity, which is achieved by applying a linear, concave or convex gradient or a stepwise gradient to the quantitative composition.

The eluate fractions can be tested for the presence of the glycolipids and their content and purity by various methods. The colour reactions and staining methods characteristic for glycolipids or glycosphingolipids and described in the experimental section are suitable for this. The fractions can be further separated, in a suitable mobile phase, on thin layer plates or films coated with silica gel, $C_{18}$-alkane derivatives of silica gel, polyamide, cellulose or polyacrylamide. The substances separated are eluted from the plate or film with a non-aqueous solvent, for example a mixture of chloroform and methanol, and subjected to investigations by means of thin layer chromatography, hydrolysis and analysis of the hydrolysis products, gas chromatography, mass spectrometry, determination of the shortening of the healing time of surface lesions on mammals or observation of the behaviour of cell cultures to which these substances are made available. The results show that the active compounds are glycosphingolipids.

It was possible to demonstrate, by the pharmacological experiments described below, that the active compounds obtained have both a marked proliferation-promoting influence on previously damaged fibroblasts in vitro and a regeneration-promoting effect on corresponding cell populations in vivo. It is clear that the substances are not just the usual substances having a mitotic action, since healthy cell cultures kept under normal conditions show no changes when the substances mentioned are added. In contrast, cultures which have been previously damaged by various harmful agents and have an abnormally low rate of division are brought back to a normal rate of division virtually identical to that of a healthy culture within a short time.

Because of the fact that the repair mechanisms of damaged cell populations are stimulated both in vitro and in vivo by the substances prepared according to the invention, these are suitable for therapeutic use, especially on wounds or ulcerations which heal slowly or badly and which have a restricted repair capability.

The promoting action of these substances on the healing of wounds can be demonstrated by the following animal experiments.

EXPERIMENT 1

The skin hair of anaesthetised rats is removed and a burn wound is made on both sides of their trunk by application of a brass disc with a diameter of 2 cm and with a temperature of 270° C. for 30 seconds. The active compounds are incorporated into a jelly base so that a 20% strength treatment jelly is formed. As a control, water or physiological saline solution is incorporated. Groups of 10 animals with 2 wounds are treated locally twice daily with the jelly, and the time taken for final healing is recorded. The substance with the $R_f$ value of 0.65 described in Example 2 shortens the healing time by up to 21% in comparison with the control group.

EXPERIMENT 2

In each case four burn wounds are made dorsally on minipigs as described in Experiment 1, and 4 stamp wounds 2.5 cm in diameter are made with a hollow cylindrical borer. The active compounds are incorporated into a jelly base up to a content of 20%. The wounds are brushed twice daily with the jelly and the time taken for final healing is recorded. The substance with the $R_f$ value of 0.65 shortens the healing time by 18%.

EXPERIMENT 3

Burn wounds are made on minipigs as described in Experiment 1. After daily treatment of the wound for 6, 12, 18 and 22 days, animals are removed from the treatment group and sacrificed under anaesthetic. The wounds are cut out, dissected and fixed in 4% strength buffered formalin. These pieces of tissue are processed to histological paraffin sections $4\mu$ thick. The following parameters are determined quantitatively:
1. Length of the epithelialised wound surface
2. Length of the non-epithelialised wound surface
3. Length of the stratum basale of the epidermis
4. Area of newly formed epidermis
5. Area of hair follicles and sebaceous glands Evaluation of the parameters shows that the purified substance described in Examples 2 to 6 accelerates the formation of epithelial tongues and their migration towards the centre of the wound in comparison with the control animals. The accelerating action on the healing of the wounds manifests itself predominantly in the early phase of the development of a stroma, the stratum basale and the papillae.

EXPERIMENT 4

Stamp wounds 1 cm wide and 5 mm deep are made on anaesthetised rats. Hollow cylindrical sponges of viscose cellulose are inserted into these wound holes. 100 $\mu$l of purified substance are introduced daily into the internal hollow of the cylinder. The sponges are removed 4, 10, 16 and 21 days after implantation and are investigated for their content of haemoglobin, deoxyribonucleic acid and hydroxyproline. On days 4 and 10 after the implantation, the content of haemoglobin, deoxy-RNA and hydroxyproline in the implanted sponges in the wounds which have been treated with the purified substances is no higher than that in the control animals, but on days 16 and 21, these sponges have a significantly higher haemoglobin, DNA and hydroxyproline content. As regards the method, see J. Niinikoski and S. Renvall, Acta Chir. Scand.145 (1979), 287–291.

The healing of the wounds is accelerated by the purified substances from Examples 2 to 6 in the early development of stroma and stratum basale with capillaries.

EXPERIMENT 5

The growth of cell cultures, for example growing fibroblasts, can be inhibited by leaving sodium bicarbonate out of the nutrient medium. The addition of the substances described in Examples 2 to 6 to the nutrient medium means that the cells recover from this inhibiting action more rapidly and reach the normal rate of division again considerably earlier than the correspondingly inhibited but untreated cell cultures.

The numerical data in respect of mixtures of solvents in the examples always relate to volumes; for example, ether:ethanol=3:1 denotes a mixture of 3 parts by volume of ether and 1 part by volume of ethanol.

EXAMPLE 1

Calf blood obtained from slaughtered animals is immediately mixed with ethanol up to a concentration of 20% at the place of slaughter, and the mixture is treated with the bacteriostatic agents methyl p-hydroxybenzoate (methylparaben) and n-propyl p-hydroxybenzoate (propylparaben) up to a concentration of in each case 0.02%. The blood is subjected to autolysis at room temperature for 3 days, during which severe haemolysis and partial degradation of unstable constituents take place and membrane components are dissolved out of the membranes. This autolysis product is separated from the sediment by decanting and the supernatant liquor is dialysed, statically or dynamically, through a membrane with an exclusion limit of 10,000 for 3 days. In dynamic dialysis, dialysate and counter-dialysate are pumped through the dialysis membrane in a countercurrent process for 3 days, so that as high as possible a concentration gradient always exists.

The resulting counter-dialysate has a dry weight of 5 to 80 mg/ml and contains an amount of up to 1 mg/ml of substances which promote the healing of wounds. In the process according to the abovementioned European patent application, an amount of 0.005 mg/ml of corresponding glycosphingolipids is obtained.

EXAMPLE 2

2 liters of calf blood are mixed with 300 ml of ethanol and are subjected to autolysis at room temperature for three days. The autolysis product is filtered through an ultrafilter with an exclusion limit of 10,000 (molecular weight) and is thereby separated from cell fragments and large proteins. The filtrate is mixed with 6 liters of ethanol:ether in a ratio of 3:1, whereupon a precipitate consisting chiefly of glycosphingolipids is formed. The precipitate is sedimented by centrifugation at 18,000 g for 30 minutes, and is separated from the liquid phase.

The precipitate is dried in vacuo at 37° C. and dissolved in 20 ml of chloroform:methanol in a ratio of 65:35. The dissolved glycosphingolipids are separated by chromatography over a Florisil column (trade name; magnesium silicate gel, highly selective adsorbent from Messrs. Floridin Corp., Pittsburg, Pa., U.S.A.) which is 5.0 cm in diameter and 40 cm in length and is equilibrated with chloroform:methanol in a ratio of 65:35, remaining phospholipide thereby being removed. The glycosphingolipids are eluted via a stepwise gradient of in each case 2 liters of 35%, 50% and 75% of methanol in chloroform and finally with 100% of methanol. The substances obtained in the elution stages are subjected to the wound healing test described in the introduction, and it is found that the last fraction (eluted with 100% of methanol) contains the substances which accelerate the healing of wounds.

The substances contained in this fraction are applied to preparative silica gel thin layer plates with a layer thickness of 2 mm and are subjected to ascending chromatography, over a zone of 18 cm, in the mobile phase chloroform:methanol:0.1% strength $CaC_{l2}$ in water=55:45:10. After the chromatography, the plates are dried and are briefly placed in a chamber with a saturated iodine atmosphere. The zones thereby stained yellow are marked, scraped off, after sublimation of the iodine, and eluted from silica gel using chloroform:methanol=50:50. Experiments to determine the shortening of the healing time for burn wounds on rats give positive results with the fraction which has the $R_f$ value of 0.65 in the thin layer chromatography separation process mentioned.

EXAMPLE 3

2 liters of counter-dialysate from Example 1 are evaporated to dryness on a rotary evaporator or by lyophilisation and the residue is taken up in 4 liters of tetrahydrofuran:0.01M KCl in a ratio of 4:1. Insoluble material is separated off via a paper filter and the clear solution is concentrated to 500 ml on a rotary evaporator. 1 liter of chloroform:methanol in a ratio of 2:1 is added and the organic and aqueous phases are separated by addition of 200 ml of water. The upper phase, which contains the glycolipids, is separated off and concentrated to dryness. The dry substance is dissolved in 10 ml of chloroform:methanol:water=90:10:0.2 and the solution is applied to a column of Bio-Sil A which is 1.5 cm in diameter and 120 cm in length and is equilibrated with chloroform:methanol:water=90:10:0.2. The column is washed with 1.5 liters of the same mobile phase and the glycolipid is then eluted from the column with 1 liter of chloroform:methanol:water=85:15:0.2. The substance purified by this process is a glycolipid which shortens the healing time of wounds.

EXAMPLE 4

2 liters of counter-dialysate from Example 1 are extracted with ethanol:ether in a ratio of 3:1 as described in Example 2, and the precipitate is taken up in 20 ml of chloroform:methanol=2:8. Diethylaminoethyl-Sephadex A50 in the $Cl^-$ form is brought into the acetate form by washing with 0.1N sodium hydroxide solution and 1N acetic acid, and is washed with methanol and filled into a column 2.5 cm in diameter and 20 cm in length. The material dissolved in chloroform:methanol=2:8 is applied to the column and the column is washed with in each case 200 ml of 0.01M sodium acetate, 0.02M sodium acetate and 0.2M sodium acetate. The glycolipid is then eluted with chloroform:methanol in a ratio of 2:8.

The glycolipid eluted by this process shortens the healing time of burn wounds.

EXAMPLE 5

200 ml of counter-dialysate from Example 1 are concentrated to dryness in a rotary evaporator or by lyophilisation, and the residue is dried over phosphorus pentoxide in a desiccator for at least 3 hours. 15 ml of a freshly prepared 20% strength solution of benzoic anhydride in pyridine are added to the dry material, followed by 15 ml of a 10% strength solution of p-dimethylaminopyridine in pyridine. The vessel is closed tightly and incubated at 37° C. for 2 hours. The vessel is cooled and the contents are separated from the insoluble material via a filter or by centrifugation.

The pyridine is removed in a stream of nitrogen and the dry material is taken up in 30 ml of hexane. The hexane is washed three times with in each case 18 ml of alkaline methanol-water solution consisting of 0.4 g/100 ml of sodium carbonate in methanol:water=80:20. The hexane phase is dried under nitrogen and taken up in 4% of ethyl acetate in hexane.

The per-O-benzoylated glycolipid is eluted over a high pressure liquid chromatography silica gel column with a gradient of from 4% to 45% of ethyl acetate in hexane. The per-O-benzoylated glycolipid isolated by this process is hydrolysed in 0.6N sodium hydroxide solution at 37° C. for 1 hour in order to remove the benzoyl groups. The hydrolysate is mixed with 5 volumes of acetone and the natural glycolipid which has precipitated is filtered off or centrifuged.

The glycolipid purified by this process shortens the healing time of burn wounds.

EXAMPLE 6

9 volumes of ethanol are added to the dialysate and the mixture is stirred at 85° C. for 30 minutes. The precipitate thereby formed is removed over filter paper and the clear solution is stored at −20° C. for three days. The desired substance precipitates and sediments during this period. The supernatant liquor is decanted, the sediment is taken up in chloroform:methanol=2:1 and the mixture is applied to a diethylaminoethyl-Sephacel column in the acetate form. The column is eluted with chloroform:methanol=2:1 and the eluate is collected. This is dried in a rotary evaporator and the residue is dissolved in chloroform. The solution is applied to a column filled with activated silica gel in chloroform. The column is rinsed first with chloroform and then with chloroform:methanol=9:1 and these eluates are discarded. The column is then rinsed with acetone:methanol=9:1, and this fraction contains the desired glycolipids in pure form.

CHARACTERISATION OF THE SUBSTANCE

The substance purified according to Example 2 is separated by chromatography on thin layer silica gel plates in the mobile phase methanol:chloroform:0.1% of $CaCl_2$ in water=55:45:10.

A mixture of the following substances is simultaneously separated, as comparison substances: asialoganglioside$_{M1}$, abbreviated to Asialo-$G_{M1}$ in the following text, Asialo-$G_{M2}$, Asialo-$G_{M3}$, Asialo-$G_{D1a}$, cerebroside and psychosine.

The plates are stained by the following methods:

1. 20 mg of cresyl violet in 1,000 ml of 1% strength acetic acid; blue-violet coloration.

2. 1% of diphenylamine in 2 ml of ethanol, 100 ml of concentrated hydrochloric acid and 80 ml of acetic acid; red coloration.

3. Spray first with 5.25% strength hypochlorous acid in 40 ml of benzene and 5 ml of acetic acid, dry, then 1% of benzidine in 50% strength ethanol; blue coloration.

4. 0.1 g of orcinol in 1 ml of 1% strength iron-III chloride and 50 ml of water; brown coloration.

5. The thin layer plates are exposed to iodine vapours in a chamber. The comparison substances and the substance to be analysed having an $R_f$ value of 0.65 are stained yellow.

6. If thin layer plates with a fluorescence indicator for the wavelengths 254 nm and 366 nm are used, the fluorescence is not weakened by the substance to be analysed of $R_f$ value 0.65, and also the comparison substances do not alter the fluorescence of the plates.

7. 0.2% of naphthoresorcinol in acetone and 10% strength phosphoric acid as the spray reagent. The treated plate is heated at 90° C. for 5 minutes; blue-red coloration.

8. 1 g of p-ansidine in 100 ml of 70% strength ethanol; blue coloration.

QUALITATIVE AND QUANTITATIVE DETERMINATION 1 ml of the substance purified according to Example 2 is dried in a rotary evaporator in vacuo at 37° C. or by lyophilisation. The dry substance is taken up in 0.8 ml of 2N sulphuric acid and 0.4 ml of dioxane and the mixture is sealed in ampoules. The samples are hydrolysed at 95° C. for 3 hours and are then neutralised by addition of 0.14 ml of 10N sodium hydroxide solution. The neutralized hydrolysate is buffered with 1.66 ml of 0.2M sodium borate buffer of pH 8.0 and is extracted in a separating funnel with 2.0 ml of diethyl ether for 5 minutes. The lower phase is discarded and the upper ether phase is dried in a waterbath at 37° C. The dried substance is taken up in 3 ml of chloroform using 0.0025% of fluorescamine—4-phenylspiro-[furan-2(3H)-1′-phthalane]-3,3′-dione [M. Naoi, J. C. Lee and S. Rosman, Anal. Biochem. 58 (1974), 571–577] —and the components are mixed for 30 seconds. The fluorescence of this solution is measured at an excitation wavelength of 385 nm and an emission wavelength of 480 nm.

We claim:

1. A process for the preparation of cell- and tissue-regenerating substances of the glycolipid series from blood or organ homogenates from mammals, comprising subjecting the blood or organ homogenate to autolysis and dialysis against an alcoholic-aqueous medium, the autolysis and dialysis being carried out simultaneously and continuously, in a countercurrent process.

2. A process according to claim 1, wherein bovine or calf blood is used as the starting material.

3. A process according to claim 1, wherein the glycolipids are precipitated from the resulting dialysis by adding ethanol and leaving the ethanolic solution formed to stand at a temperature in the range from −15° to −25° C., and the glycolipids are separated off.

4. A process according to claim 1, wherein the resulting dialystate is separated into solid/liquid or liquid/liquid phases by addition of a solvent or solvent mixture which is water-immiscible or water-miscible only to a limited extent, the glycolipids passing into the solid phase or into the organic, less polar phase, and the phase containing the glycolipids is separated off.

5. A process according to claim 4, wherein said solvent or solvent mixture is selected from the group consisting of ethers, hydrocarbons, halogenated hydrocarbons, alcohols, carboxylic acid esters and mixtures thereof, which are water-immiscible or water-miscible only to a limited extent.

6. A process according to claim 1, wherein calf blood is used as the starting material.

7. A process according to claim 4, wherein said glycolipids pass into said organic phase, which is then dried under mild conditions.

8. A method according to claim 1, further comprising recovering the glycolipid.

* * * * *